(12) United States Patent
Homer

(10) Patent No.: US 9,204,931 B2
(45) Date of Patent: Dec. 8, 2015

(54) HYPOPIGMENTATION TATTOOING

(76) Inventor: Gregg S. Homer, Laguna Beach, CA (US)

(*) Notice: Subject to any disclaimer, the term of this patent is extended or adjusted under 35 U.S.C. 154(b) by 545 days.

(21) Appl. No.: 13/458,117

(22) Filed: Apr. 27, 2012

(65) Prior Publication Data
US 2013/0289671 A1   Oct. 31, 2013

(51) Int. Cl.
| | | |
|---|---|---|
| A61B 18/18 | (2006.01) | |
| A61B 18/20 | (2006.01) | |
| A61N 5/02 | (2006.01) | |
| A61N 5/06 | (2006.01) | |
| A61N 7/00 | (2006.01) | |
| A61B 18/00 | (2006.01) | |
| A61N 5/067 | (2006.01) | |

(52) U.S. Cl.
CPC ....... *A61B 18/203* (2013.01); *A61B 2018/0047* (2013.01); *A61N 5/02* (2013.01); *A61N 5/0616* (2013.01); *A61N 7/00* (2013.01); *A61N 2005/067* (2013.01); *A61N 2005/0659* (2013.01); *A61N 2005/0663* (2013.01); *A61N 2007/0034* (2013.01); *A61N 2007/0086* (2013.01)

(58) Field of Classification Search
CPC ................... A61B 18/203; A61B 2018/00452; A61B 2018/00476
USPC ............................. 606/2, 3, 9–13; 607/88–90
See application file for complete search history.

(56) References Cited

U.S. PATENT DOCUMENTS

| | | | | |
|---|---|---|---|---|
| 7,029,469 | B2* | 4/2006 | Vasily | 606/9 |
| 2002/0113575 | A1* | 8/2002 | Lee | 320/132 |
| 2005/0065503 | A1* | 3/2005 | Anderson et al. | 606/9 |
| 2011/0257642 | A1* | 10/2011 | Griggs, III | 606/22 |

OTHER PUBLICATIONS

Gupta et al., Depigmentation therapies in vitiligo, Indian Journal of Dermatology, Venereology and Leprology, vol. 78, No. 1, Jan.-Feb. 2012, pp. 49-58.*

* cited by examiner

*Primary Examiner* — William Thomson
*Assistant Examiner* — John R Downey

(57) ABSTRACT

The present invention is directed to a method for creating permanent or semi-permanent images on a pre-determined treatment area of the skin wherein electromagnetic radiation ("EMR") is applied to the treatment area. Based on the EMR energy density selected, no hypertrophic scarring occurs. The skin is nevertheless hypopigmented where the spot is directed. When the treated area is tanned, the selected image appears. When the skin is pale, the selected image does not appear.

30 Claims, 2 Drawing Sheets

Upper Arm Hyperpigmentation Laser Tattoo Scan

* EMR device optionally includes electronic guidance system and/or computer-guided tracking system, as described in specification.

Fig. 1 - Upper Arm Hyperpigmentation Laser Tattoo Scan

* EMR device optionally includes electronic guidance system and/or computer-guided tracking system, as described in specification.

Upper Arm Hyperpigmentation
Laser Tattoo Scan

HYPOPIGMENTATION TATTOOING

BACKGROUND OF THE INVENTION

Tattoos have been popular throughout history. Otzi the Iceman (c. 3300 BCE) had 57 separate tattoos. See Callaway, World's Oldest Tattoos Were Made of Soot, New Sci. (Jul. 15, 2009). A tattooed mummy (c. 300 BCE) was extracted from the permafrost of Altaï in the second half of the 15th century. Badenkov, Altai Mountain Knot: Between Conservation and Development, in Connectivity Conservation Management: A Global Guide 246 (Worboys, et al. eds. 2010).

Since the 1990s, tattoos have become a mainstream part of global and Western fashion, common among both sexes, to all economic classes, and to age groups from the later teen years to middle age. Tattoos have been particularly popular in America. In 2008, 14 percent of all adults in the United States had a tattoo, slightly down from 2003, when 16 percent had a tattoo. Among age groups, 9 percent of those ages 18-24, 32 percent of those 25-29, 25 percent of those 30-39 and 12 percent of those 40-49 have tattoos, as do 8 percent of those 50-64. Men were slightly more likely to have a tattoo than women (15 percent versus 13 percent). See Harris Interactive, Three in Ten Americans with a Tattoo Say Having One Makes Them Feel Sexier or More Artsy (Feb. 12, 2008). And the trend is not limited to America. In 2010, 25 percent of Australians under age 30 had tattoos. See Stack, I'm Inked Therefore I Am: Why Tatts Have Left a Mark on Gen Y, Sun. Tele. (Oct. 31, 2010). And in 2011, even Barbie—sold throughout the industrialized world—donned tattoos. See Krupnick, Tokidoki Barbie Features Tattoos, Pink Hair, The Huffington Post (Oct. 19, 2011).

The traditional method of tattooing involves placing pigment into the skin's dermis, the tissue layer below the epidermis. The body then detects the presence of the foreign pigment material, and the immune system discharges phagocytes to engulf the pigment particles. The engulfed particles then remain lodged in the layer just below the boundary between the dermis and the epidermis. See Suthamjariya, Lasers in Dermatology 40-17, in Biomedical Photonics Handbook (Vo-Dinh ed. 2003).

There are at least two shortcomings with the traditional method of tattooing—regret, and safety. Although the majority of people who get tattoos do not regret doing getting tattoos, about 16 percent want to remove them (see Harris Interactive, supra), and removal is both painful and expensive. The principal reasons given by patients for tattoo removal are moving on from the past, problems wearing clothes, embarrassment, and concerns that tattoos could adversely affect job or career. See Armstrong, et al., Motivation for Contemporary Tattoo Removal, 144 Arch. Dermatol. 879-84 (2008).

The markets for both getting and removing tattoos tend to be seasonal. The preference for getting tattoos is highest in the summer, when people tend to wear less clothing, get more tanned, are more conscious of their bodies and what they communicate to others, and want to feel sexier. See Divito, Summer is Tattoo Season, The Associated Press (Jun. 17, 2007) ("It's summer, and that means it's tattoo season, the best time of the year to show off—or take in—all that sexy ink"); Harris Interactive, supra. The preference for removing tattoos, however, is highest in the winter, when people tend to wear more clothing, work more, be less conscious of their bodies and what they communicate to others, care less about feeling sexier, and be more concerned about how tattoos might adversely affect job or career. See Saint Louis, A Change in Season and Regimen, NYT (Nov. 10, 2010); Armstrong, supra.

There other shortcomings concerns the many health risks associated with tattoos. Allergic and lichenoid reactions, for example, can occur from any of the classic pigments and their degradation products. See Kaatz, Body-Modifying Concepts and Dermatologic Problems: Tattooing and Piercing, 26 Clinics Dermatol. 35-44 (2008). Delayed contact urticaria has also been reported. See Bagnato, et al., Urticaria in a Tattooed Patient, 27 Allergol. Immunopathol. 32-33 (1999). On occasion, morphealike lesions (see Mahalingam, et al., Morphea-Like Tattoo Reaction, 24 Am. J. Dermatopathol. 392-95 [2002]) and marked pseudoepitheliomatous hyperplastic lesions (Balfour, et al., Massive Pseudoepitheliomatous Hyperplasia: An Unusual Reaction to a Tattoo, 25 Am. J. Dermatopathol. 338-40 [2003]) have been reported.

Another risk is infection—both bacterial and viral. Severe systemic bacterial infections after tattooing include sepsis, endocarditis, and spinal and epidural abscesses, by *Streptococcus pyogenes, Staphylococcus aureus*, or *Pseudomonas*. See Satchithananda, et al., Bacterial endocarditis following repeated tattooing, 85 Heart 11-12 (2000). Infection with *Treponema pallidum* and typical or atypical mycobacteria has also been reported. See Long & Rickmann, Infectious Complications of Tattoo, 18 Clin. Infect. Dis. 610-19 (1994). Viral infections include hepatitis B and C, HIV, papilloma, and mollusca contagiosa. See Perez, et al., Molluscum Contagiosum on a Multicoloured Tattoo, 20 J. Eur. Acad. Dermatol. Venereol. 214-38 (2006); Nishioka & Gyorkos, Tattoos As Risk Factors for Transfusions Transmitted Diseases, 5 Int'l J. Infect. Dis. 27-34 (2001); Haley & Fischer, Commercial Tattooing as a Potentially Important Source of Hepatitis C Infection, 80 Medicine 134-51 (2000); Doll, Tattooing in prison and HIV infection, 1 Lancet 66-67 (1988).

One of the most dangerous health risks from tattooing is malignant tumors, including malignant melanoma (see Kircik, et al., Malignant Melanoma in a Tattoo, 32 Int'l J. Dermatol. 297-98 [1993]), basal cell carcinoma (see Doumat, et al., Basal Cell Carcinoma in a Tattoo, 208 Dermatol. 181-82 [2004]), squamous cell carcinoma (see McQuarrie, Squamous-Cell Carcinoma Arising in a Tattoo, 49 Minn. Med. 799-801 [1966]), and primary non-Hodgkin lymphoma (see Armiger & Caldwell, Primary Lesion of a Non-Hodgkin's Lymphoma Occurring in a Skin Tattoo: Case Report, 62 Plast. Reconstr. Surg. 125-27 [1978]).

An alternative to traditional tattooing, cryogenic hypopigmentation, involves applying a protective design template to the skin and then using a cryogenic agent (such as liquid nitrogen) to freeze the exposed portions of the skin, thereby destroying the dermal melanocytes and hypopigmenting the exposed tissue. See Method for Producing a Permanent or Nearly Permanent Skin Image, Design or Tattoo by Freezing the Skin, U.S. Patent Publication No. 20110257642 (published Oct. 20, 2011) (Charles Sherman Griggs, III, applicant). From a health perspective, the abandonment of pigments could overcome many of the serious health risks associated with traditional tattooing. The use of cryogen agents, however, poses a whole new set of health risks including thermal burns, frostbite, skin adhesion to frozen metals and skin tears, asphyxiation, toxicity, and explosion due to rapid expansion.

From a regrets perspective, the cryogenic hypopigmentation approach may be more appealing because a hypopigmented design on the skin will tend to be more apparent on tanned skin on the summer—when the preference for getting tattoos is highest—and less apparent on pale skin in the winter—when regrets and the associated preference for removing tattoos is highest. On the other hand, it is difficult to achieve highly detailed designs with cryogenic hypopigmentation. The templates can only accommodate a limited amount of detail, so this approach will be limited to simpler, grosser designs, which will tend to me less unique and less appealing. In addition, it is difficult to restrict the effects of dermal freezing to the exposed tissue, as it tends to bleed under the borders of the template. The borders of the design will therefore be uneven and imprecise, thereby producing a less appealing design. As a result, regrets and removal may run just as with this approach as with the traditional tattooing approach.

There is therefore a need for a method of tattooing that reduces or eliminates the safety risks of tattoo needles, tattoo pigments, and cryogenic agents, as well as the regrets from the winter design visibility of traditional tattoos and the lack of refinement of cryogenic hypopigmentation.

BRIEF SUMMARY OF THE INVENTION

The present invention is directed to a method for creating permanent or semi-permanent images on a pre-determined treatment area of the skin wherein electromagnetic radiation ("EMR") is applied to the treatment area. In one embodiment of the invention, an image of a ship's anchor bearing the name "Sophie" is selected. The treatment area is approximately 6 cm×4 cm located the patient's upper arm. The patient is instructed to tan the treatment area for one week prior to treatment. A topical anesthetic (lidocaine hydrochloride) is applied to the treatment area one hour before treatment. A laser is used. The laser is guided by a computer-driven scanner. The selected image has been programmed into the scanner software by any one of a number of methods well-known in the art. The patient's arm is secured. The laser beam is fired in a raster pattern. An acousto-optical modulator is used to blank the beam as directed by the scanner software to yield the selected image. Based on the laser energy density selected, no hypertrophic scarring occurs. The skin is nevertheless hypopigmented where the spot is directed. When the treated area is tanned, the selected image appears. When the skin is pale, the selected image does not appear.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
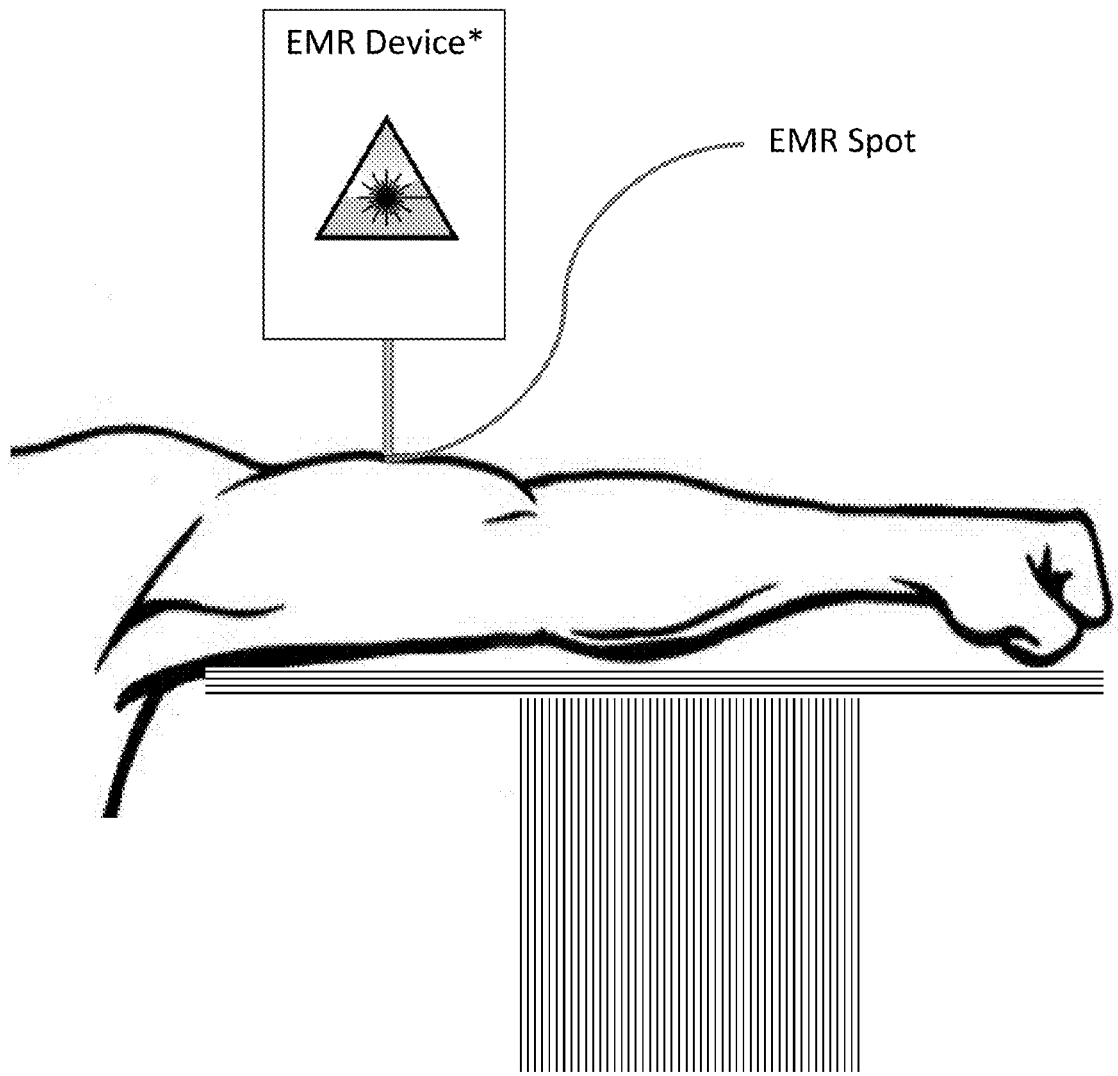
FIG. 1 shows one embodiment of the invention, whereby the patient's arm is secured for treatment.
Figure 2:
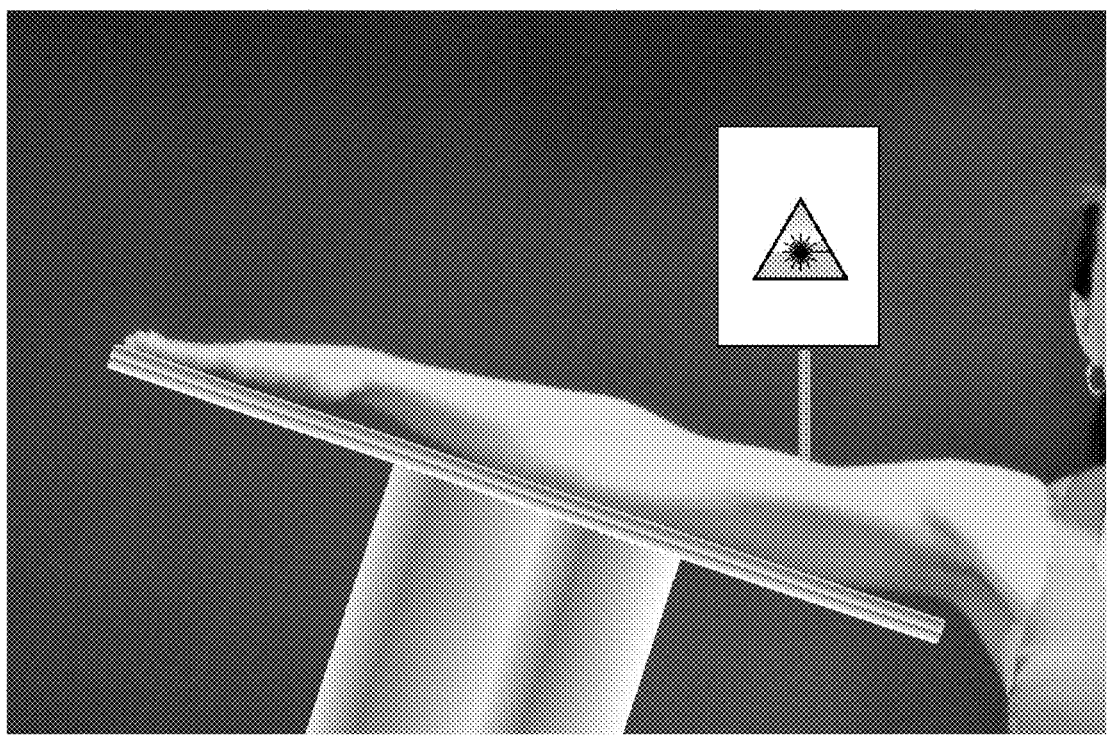

The present invention is directed to a method for creating permanent or semi-permanent images on a pre-determined treatment area of the skin wherein electromagnetic radiation ("EMR") is applied to the treatment area.

As used in this disclosure, "EMR" includes any form of electromagnetic radiation, whether in the form of sound, heat, light, or otherwise, and whether consisting of radio frequency, ultrasound, microwave, infrared, visible light, ultraviolet, x-ray, t-ray, gamma ray, or otherwise. The term "EMR" is not intended to restrict the form of radiation in terms of monochromaticity (i.e., composed of one or more than one different wavelength), directionality (i.e., produce a single non-divergent spot or radiate in several different directions), or coherence (i.e., the waves produced consist of a single phase relation or of multiple phase relations). Moreover, the frequency of the EMR can be any frequency within the EMR spectrum, including, without limitation, extremely low frequency sound radiation (with a frequency of 3 Hz) to gamma radiation (with a frequency of 300 EHz). The EMR can be delivered in a continuous wave or in pulses, and the pulse width may be any time interval, including microseconds, nanoseconds, picoseconds, femtoseconds, or attoseconds. If pulsed, any repetition rate may be used, including, without limitation, repetition rates from 1 hertz to 100 terahertz. In addition, any energy output may be used, and any energy density may be created at the target treatment side, including, without limitation, energy outputs from 1 watt to 1000 watts. Finally, any gain medium may be used, including, without limitation, glass, solid, liquid, gas, crystal, or semiconductor. In the case of laser energy, the specific gain media may comprise Nd:YAG, alexandrite, ruby, pulsed-dye, or any other medium.

The term "beam" includes any EMR pathway, such as a laser beam, radio frequency pathway, ultrasound pathway, microwave pathway, infrared pathway, visible light pathway, ultraviolet pathway, x-ray pathway, t-ray pathway, gamma ray pathway, or otherwise. In addition, the beam may be fully collimated or any drainage angle of divergence or convergence. Finally, the term "beam" should be understood to include a single beam or multiple beams, and the multiple beams may result from the splitting or screening of a single beam or the generation of multiple beams with multiple frequencies, shapes, energy densities, and other characteristics. If the beam is a laser beam, it may or may not be fired through a goniolens.

The term "spot" includes the plane of intersection between the beam and the target cells or tissue, such as the laser spot, radio frequency site, ultrasound site, microwave site, infrared site, visible light site, ultraviolet site, x-ray site, t-ray site, gamma ray site, or otherwise. The term "EMR" is not intended to limit the beam or spot to any particular shape, size, or angle of projection. Spots can be tangent, overlapped, or isolated, and overlapping may occur in any direction (x, y, or z). They can also be square, rectangular, circular, elliptical, triangular, trapezoidal, torus, or otherwise. Finally, they can measure 1 microns (μ) to 20 millimeters or otherwise.

Movement of the beam may be guided by a computerized scanning system. Such systems are well-known in the art. See, e.g., LAPG High Speed Scanner (Sciton, Inc., Palo Alto, Calif., USA). The scanning system can be implemented using one or more computer systems. An exemplary computer system can include software, monitor, cabinet, keyboard, and mouse. The cabinet can house familiar computer components, such as a processor, memory, mass storage devices, and the like. Mass storage devices may include mass disk drives, floppy disks, Iomega ZIP™ disks, magnetic disks, fixed disks, hard disks, CD-ROMs, recordable CDs, DVDs, DVD-R, DVD-RW, Flash and other nonvolatile solid-state storage, tape storage, reader, and other similar media, and combinations of these. A binary, machine-executable version, of the software of the present invention may be stored or reside on mass storage devices. Furthermore, the source code of the software of the present invention may also be stored or reside on mass storage devices (e.g., magnetic disk, tape, or CD-ROM). Furthermore, a computer system can include subsystems such as central processor, system memory, input/output (I/O) controller, display adapter, serial or universal serial bus (USB) port, network interface, and speaker. The present invention may also be used with computer systems with additional or fewer subsystems. For example, a computer system could include more than one processor (i.e., a multiprocessor system) or a system may include a cache memory. The beam may be guided in any shape or pattern, including, without limitation, a spiral pattern, a raster pattern, or a segregated regional pattern.

Computer-guided tracking may be used to follow the treatment areas in the x, y, or z directions (active tracking) or interrupt transmission (passive tracking) if the treatment area moves during treatment. Computer-guided tracking systems are well-known in the art. See, e.g., Intelligent Optical Tracking System (Solta Medical, Inc., Hayward, Calif., USA).

In one embodiment of the invention, an image of a ship's anchor bearing the name "Sophie" is selected. The treatment area is approximately 6 cm×4 cm located the patient's upper arm. The patient is instructed to tan the treatment area for one week prior to treatment. A topical anesthetic (lidocaine hydrochloride) is applied to the treatment area one hour before treatment. A Q-switched, frequency-doubled (532 nm), single-pulse, Nd:YAG laser is used. The laser produces a circular spot with a diameter of 1 mm and an energy density of 3.5 J/cm^2. The beam is collimated. The pulse width is 10 ns. The laser is guided by a computer-driven scanner. The selected image has been programmed into the scanner software by any one of a number of methods well-known in the art. The patient's arm is secured. See FIG. 1. The laser beam is fired in a raster pattern at a repetition rate of 5 kHz, with the angle of the beam approximately perpendicular to the treatment surface. An acousto-optical modulator is used to blank the beam as directed by the scanner software to yield the selected image. The spot separation is 500μ (i.e., 50% overlap along x), and the line separation is 1 mm (i.e., 0% overlap along y). Computer-guided tracking is used to ensure consistency of treatment even if the patient moves during treatment. Based on the laser energy density selected, no hypertrophic scarring occurs. The skin is nevertheless hypopigmented where the spot is directed. When the treated area is tanned, the selected image appears. When the skin is pale, the selected image does not appear.

In another embodiment of the invention, an image of Lord Shiva is selected. The treatment area is approximately 12 centimeters×8 centimeters located the patient's upper back. The patient is instructed to tan the treatment area for one week prior to treatment. A topical anesthetic (lidocaine hydrochloride) is applied to the treatment area one hour before treatment. A Q-switched, single-pulse alexandrite laser (755 nanometers) is used. The laser produces a circular spot with a diameter of 2 millimeters and an energy density of 4.5 Joules/square centimeter. The beam is collimated. The pulse width is 100 nanoseconds. The laser is guided by a computer-driven scanner. The selected image has been programmed into the scanner software by any one of a number of methods well-known in the art. The patient's back is secured. The laser beam is fired in a raster pattern at a repetition rate of 5 kilohertz, with the angle of the beam approximately perpendicular to the treatment surface. An acousto-optical modulator is used to blank the beam as directed by the scanner software to yield the selected image. The spot separation is 1 millimeter (i.e., 50 percent overlap along x), and the line separation is 2 millimeters (i.e., 0 percent overlap along y). Computer-guided tracking is used to ensure consistency of treatment even if the patient moves during treatment.

One of ordinary skill in the art would recognize many other variations, modifications, and alternatives. The above examples are merely illustrations, which should not unduly limit the scope of the claims herein. It is also understood that the examples and embodiments described herein are for illustrative purposes only and that various modifications or changes in light thereof will be suggested to persons skilled in the art and are to be included within the spirit and purview of this application and scope of the appended claims.

The invention claimed is:

1. A method for creating a pre-selected hypopigmented image on a skin surface, comprising:
   using an electromagnetic radiation device to apply an electromagnetic radiation spot on the skin surface,
   wherein the device and the spot are configured to hypopigment the skin surface where the spot is applied, and
   a computer-driven scanner is configured to guide the spot about the skin surface in a pre-determined pattern, hypopigmenting the skin surface where the spot is applied and creating the preselected hypopigmented image on the skin surface.

2. A method for creating a pre-selected hypopigmented image on a skin surface, comprising:
   providing an electromagnetic radiation device,
   wherein the device is configured to apply an electromagnetic radiation spot on the skin surface,
   the device and the spot are further configured to hypopigment the skin surface where the spot is applied, and
   a computer-driven scanner is configured to guide the spot about the skin surface in a pre-determined pattern, hypopigmenting the skin surface where the spot is applied and creating the preselected hypopigmented image on the skin surface.

3. The method of claim 1 wherein the period of time during which the hypopigmented skin surface remains hypopigmented is between about three months and about 20 years.

4. The method of claim 2 wherein the period of time during which the hypopigmented skin surface remains hypopigmented is between three months and 20 years.

5. The method of claim 1 wherein the image is created on the skin surface of at least one of the arm, hand, back, breast, stomach, buttocks, leg, foot, or head.

6. The method of claim 2 wherein the image is created on the skin surface of at least one of the arm, hand, back, breast, stomach, buttocks, leg, foot, or head.

7. The method of claim 1 wherein the device comprises a laser.

8. The method of claim 2 wherein the device comprises a laser.

9. The method of claim 7 wherein the laser comprises a gain medium, and the gain medium comprises alexandrite.

10. The method of claim 8 wherein the laser comprises a gain medium, and the gain medium comprises alexandrite.

11. The method of claim 7 wherein the laser comprises a gain medium, and the gain medium comprises a neodymium-doped crystal.

12. The method of claim 8 wherein the laser comprises a gain medium, and the gain medium comprises a neodymium-doped crystal.

13. The method of claim 7 wherein the laser comprises a gain medium, the gain medium comprises Nd:YAG, and the wavelength generated by the Nd:YAG gain medium is doubled to 532 nanometers.

14. The method of claim 8 wherein the laser comprises a gain medium, the gain medium comprises Nd:YAG, and the wavelength generated by the Nd:YAG gain medium is doubled to 532 nanometers.

15. The method of claim 7 wherein the laser comprises a gain medium, and the gain medium comprises ruby.

16. The method of claim 8 wherein the laser comprises a gain medium, and the gain medium comprises ruby.

17. The method of claim 7 wherein the wavelength generated by the laser is between about 50 nanometers and about 2000 nanometers.

18. The method of claim 8 wherein the wavelength generated by the laser is between about 50 nanometers and about 2000 nanometers.

19. The method of claim 7 wherein the power generated by the laser is between about 0.5 joules and about 10 joules.

20. The method of claim 8 wherein the power generated by the laser is between about 0.5 joules and about 10 joules.

21. The method of claim 7 wherein energy density at at least one spot is between about 0.5 J/cm^2 and about 10.0 J/cm^2.

22. The method of claim 8 wherein the wherein energy density at at least one spot is between about 0.5 J/cm^2 and about 10.0 J/cm^2.

23. The method of claim 7 wherein diameter of at least one spot is between about 20 microns and about 1.5 centimeters.

24. The method of claim 8 wherein diameter of at least one spot is between about 20 microns and about 1.5 centimeters.

25. The method of claim 1 wherein the spot is pulsed.

26. The method of claim 2 wherein the spot is pulsed.

27. The method of claim 25 wherein the pulse width is between about 1 femtosecond and about 500 nanoseconds.

28. The method of claim 26 wherein the pulse width is between about 1 femtosecond and about 500 nanoseconds.

29. The method of claim 1, further comprising a computer-guided tracking system, which tracking system is configured to detect movement of the skin surface and modify the application of the spot to follow the skin surface.

30. The method of claim 2, further comprising a computer-guided tracking system, which tracking system is configured to detect movement of the skin surface and modify the application of the spot to follow the skin surface.

* * * * *